United States Patent
Demmer et al.

(10) Patent No.: US 7,846,888 B2
(45) Date of Patent: Dec. 7, 2010

(54) LONG LASTING DECONTAMINATION FOAM

(75) Inventors: Ricky L. Demmer, Idaho Falls, ID (US); Dean R. Peterman, Idaho Falls, ID (US); Julia L. Tripp, Pocatello, ID (US); David C. Cooper, Idaho Falls, ID (US); Karen E. Wright, Idaho Falls, ID (US)

(73) Assignee: Battelle Energy Alliance, LLC, Idaho Falls, ID (US)

( * ) Notice: Subject to any disclaimer, the term of this patent is extended or adjusted under 35 U.S.C. 154(b) by 728 days.

(21) Appl. No.: 11/349,815

(22) Filed: Feb. 7, 2006

(65) Prior Publication Data

US 2007/0185002 A1    Aug. 9, 2007

(51) Int. Cl.
  A62D 3/00   (2007.01)
  A61Q 5/02   (2006.01)
  C11D 17/00  (2006.01)

(52) U.S. Cl. .................. 510/110; 510/123; 510/131; 510/382; 510/424; 510/426; 510/428; 86/50

(58) Field of Classification Search ............. 510/110, 510/123, 131, 382, 424, 426, 428; 252/170–179; 86/50

See application file for complete search history.

(56) References Cited

U.S. PATENT DOCUMENTS

| | | | |
|---|---|---|---|
| 4,547,306 A | 10/1985 | Hase et al. | |
| 4,850,729 A | 7/1989 | Kramer et al. | |
| 5,254,290 A * | 10/1993 | Blandiaux et al. | ............ 510/417 |
| 5,562,856 A | 10/1996 | Jeschke et al. | |
| 5,670,469 A | 9/1997 | Dingus et al. | |
| 5,864,767 A | 1/1999 | Drumgoole et al. | |
| 5,866,529 A * | 2/1999 | Erilli et al. | ................. 510/425 |
| 5,972,310 A * | 10/1999 | Sachetto | ...................... 424/45 |
| 6,106,774 A * | 8/2000 | Monticello et al. | ............ 422/28 |
| 6,333,054 B1 | 12/2001 | Rogozinski | |
| 6,376,436 B1 | 4/2002 | Cronce | |
| 6,405,626 B1 | 6/2002 | Bureaux et al. | |
| 6,514,927 B2 | 2/2003 | Lang et al. | |
| 6,525,237 B1 | 2/2003 | Purdon et al. | |
| 6,723,890 B2 * | 4/2004 | Tucker et al. | ............... 588/318 |

(Continued)

FOREIGN PATENT DOCUMENTS

FR    2841802 A1 *   1/2004

OTHER PUBLICATIONS

U.S. Patent Application Serial No. entitled "Surface Decontamination Compositions and Methods," filed concurrently herewith, U.S. Appl. No. 11/350,351.

(Continued)

*Primary Examiner*—Mark Eashoo
*Assistant Examiner*—Jane L Stanley
(74) *Attorney, Agent, or Firm*—TraskBritt

(57) ABSTRACT

Compositions and methods for decontaminating surfaces are disclosed. More specifically, compositions and methods for decontamination using a composition capable of generating a long lasting foam are disclosed. Compositions may include a surfactant and gelatin and have a pH of less than about 6. Such compositions may further include affinity-shifting chemicals. Methods may include decontaminating a contaminated surface with a composition or a foam that may include a surfactant and gelatin and have a pH of less than about 6.

26 Claims, 1 Drawing Sheet

U.S. PATENT DOCUMENTS

| | | | |
|---|---|---|---|
| 6,727,314 | B2 | 4/2004 | Burghart et al. |
| 7,070,773 | B2 | 7/2006 | Conerly et al. |
| 7,662,754 | B2 * | 2/2010 | Faure et al. ............... 507/213 |
| 2003/0060517 | A1 * | 3/2003 | Tucker et al. ............... 516/38 |
| 2003/0109017 | A1 | 6/2003 | Conerly et al. |
| 2004/0265240 | A1 * | 12/2004 | Tamarkin et al. ............ 424/45 |
| 2005/0019421 | A1 | 1/2005 | Hobbs et al. |
| 2005/0069566 | A1 * | 3/2005 | Tamarkin et al. ........... 424/401 |
| 2005/0131176 | A1 | 6/2005 | Zhao |
| 2005/0239674 | A1 | 10/2005 | Dreja et al. |
| 2006/0140984 | A1 * | 6/2006 | Tamarkin et al. ........... 424/400 |
| 2006/0211592 | A1 * | 9/2006 | Faure et al. ................ 510/421 |
| 2009/0264330 | A1 * | 10/2009 | Bruckner et al. ........... 510/181 |

OTHER PUBLICATIONS

International Preliminary Report on Patentability/Written Opinion of the International Searching Authority, PCT/US2007/061298, International Filing Date Jan. 30, 2007.

PCT International Search Report for International Application PCT/US07/61295, mailed Dec. 12, 2007, 2 pages.

* cited by examiner

LONG LASTING DECONTAMINATION FOAM

GOVERNMENT RIGHTS

This invention was made with government support under Contract Nos. DE-AC07-99ID13727 and DE-AC07-05ID14517 awarded by the United States Department of Energy. The government has certain rights in the invention.

BACKGROUND OF THE INVENTION

Field of the Invention: The present invention relates generally to compositions and methods for decontaminating surfaces and, more specifically, to compositions and methods for decontamination using a composition capable of generating a long lasting foam.

State of the Art: Several countries and international groups, many of them hostile to the United States and its allies, currently possess or are seeking to develop the capability to produce nuclear, biological and/or chemical weapons of mass destruction (WMD) and the means to deliver them. Many of these countries and international groups also advocate terrorism as a means to achieve their goals. In order to respond to the threat of terrorism using WMDs, responding agencies at all levels of government (i.e., local, state, and federal) must be adequately prepared to mitigate the hazards to the public and the environment in a timely manner. A particular problem to date has been the manner of cleaning up the potentially toxic residue from terrorist events.

Radiological devices such as nuclear weapons and "dirty bombs" represent an increasingly dangerous threat to society, particularly when they contain radiological materials with long half lives. It is vital that when radiological materials are released from such devices that they be quickly and easily cleaned up. Once released, radiological materials present a decontamination problem when deposited on the surfaces of various buildings, equipment, and vehicles, or on the ground.

Biological agents are typically particulate in nature and present a significant hazard, long after an attack, through formation of secondary aerosols that mat be inhaled. Further, biological agents may adhere to surfaces or be repositioned in the underlying environment and remain hazardous if disturbed. Thus, biological materials present a continuing decontamination problem when deposited on the surfaces of various buildings, equipment, and vehicles, or on the ground.

Chemical warfare agents may also be long lasting in the environment and many classes of persistent and semi-persistent agents exist. As a consequence, chemical warfare agents may pose a continuing hazard when deposited on the surfaces of various buildings, equipment, and vehicles, or on the ground.

Clearly, there is a need for a long lasting formulation that is stable, non-toxic to personnel and the environment, and can support a variety of decontamination chemicals selected based on the contamination to be countered. Further, the formulation should be easy to transport to a site in a substantially aqueous medium and be capable of coating surfaces, including vertical surfaces, for long enough periods of time to begin effective decontamination.

BRIEF SUMMARY OF THE INVENTION

A composition for the decontamination of a contaminated surface is disclosed. The composition comprises a surfactant and gelatin and has a pH of less than about 6. The composition is capable of generating a foam and is compatible with affinity-shifting chemical (ASC) materials.

In an exemplary embodiment, a surfactant present in the composition for decontamination comprises SILV-EX®, a firefighting foam commercially available from Ansul Inc. (Houston, Tex.).

In a further exemplary embodiment, the pH of the composition for decontamination may be less than about 6. Further, the pH may be from about −0.5 to about 6. And yet further, the pH may be 0.3 or 4.5.

In another exemplary embodiment, the composition for decontamination may further comprise affinity-shifting chemical (ASC) materials.

A foam for decontamination is also disclosed. The foam comprises a surfactant and gelatin and has a pH of less than about 6.

In yet another exemplary embodiment, a surfactant present in the foam for decontamination comprises SILV-EX®, a firefighting foam commercially available from Ansul Inc. (Houston, Tex.).

In a further exemplary embodiment, the pH of the foam for decontamination may be less than about 6. Further, the pH may be from about −0.5 to about 6. And yet further, the pH may be 0.3 or 4.5.

In another exemplary embodiment, the composition for decontamination may further comprise affinity-shifting chemical (ASC) materials.

A method of decontaminating a surface is also disclosed. The method comprises treating a surface to be decontaminated with a composition according to the present invention. Examples of contamination to be treated include, but are not limited to, biological, chemical, and radiological contamination.

A method of generating a foam is also disclosed. The method comprises providing a composition according to the present invention and injecting a gas into it so as to form a foam.

A method of decontaminating a surface with a foam is also disclosed. The method comprises generating a foam with a composition according to the present invention. The method further comprises treating the surface to be decontaminated with the foam generated from the composition according to the present invention.

DETAILED DESCRIPTION OF THE INVENTION

Figure 1:
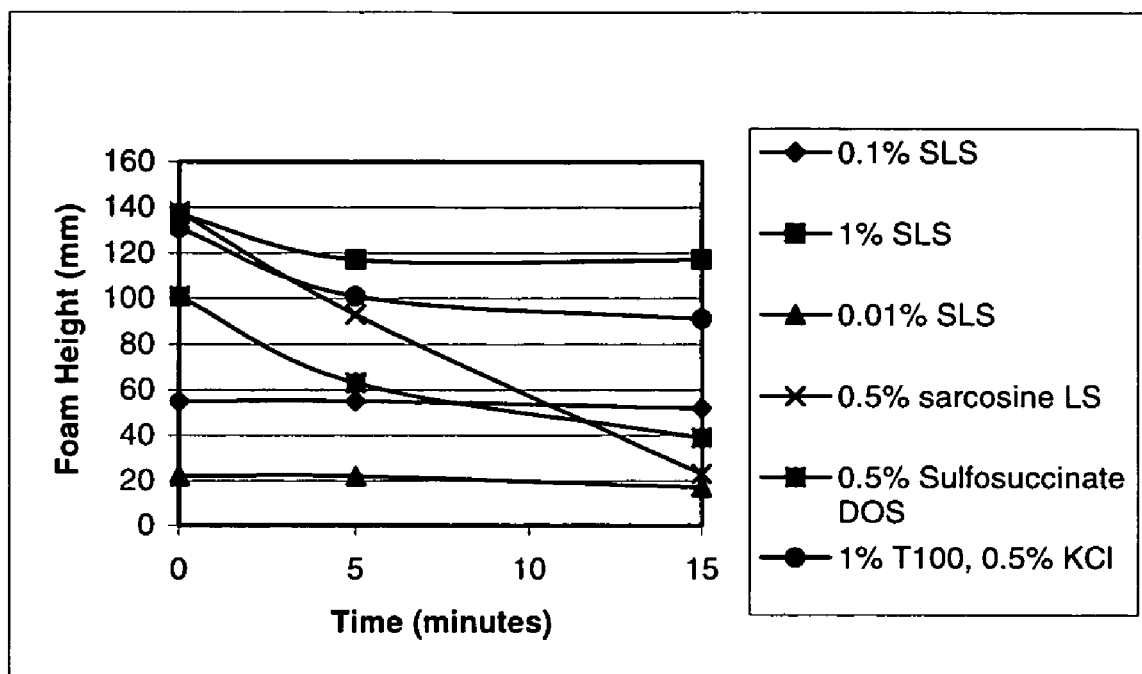
FIG. 1 is a graph depicting foam production and decay properties of various surfactants.

Before the present compositions and methods of use thereof for decontamination are disclosed and described, it is to be understood that this invention is not limited to the particular configurations, process steps, and materials disclosed herein as such configurations, process steps, and materials may vary somewhat. It is also to be understood that the terminology employed herein is used for the purpose of describing particular embodiments only and is not intended to be limiting since the scope of the present invention will be determined by the appended claims and equivalents thereof.

As used herein, "comprising," "including," "containing," "characterized by," and grammatical equivalents thereof are inclusive or open-ended terms that do not exclude additional, unrecited elements or method acts.

As used herein and in the appended claims, the singular forms, for example, "a," "an," and "the," include the plural, unless the context clearly dictates otherwise. For example, reference to "a surfactant" includes a plurality of such surfactants, and reference to a "chelator" includes a plurality of chelators, and equivalents thereof.

As used herein, "about" means reasonably close to, a little more or less than the stated number or amount, or approximately.

As used herein, "exemplary" means serving as an example of. The use of the term "exemplary" herein in connection with a particular embodiment is not to be construed as one particular embodiment being preferred over any other embodiment.

Surfactants as used herein include anionic, nonionic, cationic and/or amphoteric or zwitterionic surfactants. Examples of anionic surfactants include, but are not limited to, soaps, alkyl benzene sulfonates, alkane sulfonates, olefin sulfonates, alkyl ether sulfonates, glycerol ether sulfonates, α-methyl ester sulfonates, sulfofatty acids, alkyl sulfates, fatty alcohol ether sulfates, glycerol ether sulfates, fatty acid ether sulfates (such as sodium lauryl sulfate (SLS), ammonium lauryl sulfate (ALS), TEXAPON®, and SILV-EX®), hydroxy mixed ether sulfates, monolglyceride (ether) sulfates, fatty acid amide (ether) sulfates, mono- and di-alkyl sulfosuccinates, mono- and di-alkyl sulfosuccinamates, sulfotriglycerides, amide soaps, ether carboxylic acids and salts thereof, fatty acid isethionates, fatty acid sarcosinates, fatty acid taurides, N-acylamino acids such as, for example, acyl lactylates, acyl tartrates, acyl glutamates and acyl aspartates, alkyl oligoglucoside sulfates, protein fatty acid condensates (particularly wheat-based vegetable products) and alkyl (ether) phosphates. If the anionic surfactants contain polyglycol ether chains, they may have a conventional homolog distribution, although they preferably have a narrow-range homolog distribution. Examples of nonionic surfactants include, but are not limited to, fatty alcohol polyglycol ethers, alkylphenol polyglycol ethers, fatty acid polyglycol esters, fatty acid amide polyglycol ethers, fatty amine polyglycol ethers, alkoxylated triglycerides, mixed ethers and mixed formals, optionally partly oxidized alkenyl oligoglycosides or glucuronic acid derivatives, fatty acid-N-alkyl glucamides, protein hydrolyzates (particularly wheat-based vegetable products), polyol fatty acid esters, sugar esters, sorbitan esters, polysorbates and amine oxides. If the nonionic surfactants contain polyglycol ether chains, they may have a conventional homolog distribution, although they preferably have a narrow-range homolog distribution. Examples of cationic surfactants include, but are not limited to, quatenary ammonium compounds, for example, dimethyl distearyl ammonium chloride, and esterquats, more particularly, quaternized fatty acid trialkanolamine ester salts. Examples of amphoteric or zwitterionic surfactants include, but are not limited to, alkylbetaines, alkylamidobetaines, amino-propionates, amino-glycinates, imidazolinium betaines and sulfobetaines.

Gelatin, as used herein refers to a protein product derived through a partial hydrolysis of the collagen extracted from skin, bones, cartilage, and ligaments, etc. Gelatin is commercially available, for example, from Kraft Foods Inc. (Northfield, Ill.) under the KNOX® brand name.

Embodiments of the present invention include compositions for the decontamination of a contaminated surface. One such composition comprises a surfactant and gelatin and has a pH of less than about 6. The composition is capable of generating a foam. Examples of contamination to be treated include, but are not limited to, biological, chemical, and radiological contamination. The stable nature of the composition allows the composition to comprise any number of further chemicals and cleaning agents that would aid in the decontamination of a surface. One advantage of such a compostion is that it is made of non-toxic and environmentally friendly components. In addition, such a composition is compatible with affinity-shifting chemical (ASC) materials.

In an exemplary embodiment, a surfactant present in the composition for decontamination comprises SILV-EX®, a firefighting foam commercially available from Ansul Inc. (Houston, Tex.).

In another exemplary embodiment, the surfactant may be present in the composition for decontamination at 0.1% to 10% by weight. Further, the surfactant may be present at 1% by weight.

In an exemplary embodiment, the gelatin may be present in the composition for decontamination at 1% to 10% by weight. Further, the gelatin may be present at 3% by weight.

In a further exemplary embodiment, the pH of the composition for decontamination may be less than about 6. Further, the pH may be from about −0.5 to about 6. And yet further, the pH may be 0.3 or 4.5.

In another exemplary embodiment, the composition for decontamination may further comprise affinity-shifting chemical (ASC) materials. Examples of ASCs include, for example, a combination of acetic acid (OHAc) and sodium acetate (NaOAc) and chelators including, but not limited to, ethylenediaminetetraacetic acid (EDTA), (2-hydroxyethyl) ethylenediaminetriacetic acid (HEDTA), ethylene glycol-bis-(2-aminoethyl)-tetraacetic acid (EGTA), ammonium molybdophosphate (AMP), triethanolamine (TEA), citrate, and nitrilotriacetic acid (NTA).

Embodiments of the present invention include foam compositions for decontamination. One such foam comprises surfactant and gelatin and has a pH of less than about 6. Examples of contamination that may be treated include, but are not limited to, biological, chemical, and radiological contamination. The stable nature of the foam allows the composition to comprise any number of further chemicals and cleaning agents that would aid in decontamination. One advantage of such a foam is that it is made of non-toxic and environmentally friendly components. A further advantage is that such a foam greatly decreases the volume of solution that must be used to cover the same amount of each surface area. In addition, this foam is compatible with affinity-shifting chemical (ASC) materials.

In an exemplary embodiment, a surfactant present in the foam for decontamination comprises SILV-EX®, a firefighting foam commercially available from Ansul Inc. (Houston, Tex.).

In another exemplary embodiment, the surfactant may be present in the foam for decontamination at 0.1% to 10% by weight. Further, the surfactant may be present at 1% by weight.

In an exemplary embodiment, the gelatin may be present in the foam for decontamination at 1% to 10% by weight. Further, the gelatin may be present at 3% by weight.

In a further exemplary embodiment, the pH of the foam for decontamination may be less than about 6. Further, the pH may be from about −0.5 to about 6. And yet further, the pH may be 0.3 or 4.5.

In another exemplary embodiment, the foam for decontamination may further comprise affinity-shifting chemical (ASC) materials. Examples of ASCs include, for example, a combination of acetic acid (OHAc) and sodium acetate (NaOAc) and chelators including, but not limited to, ethylenediaminetetraacetic acid (EDTA), (2-Hydroxyethyl)ethylenediaminetriacetic acid (HEDTA), ethylene glycol-bis-(2-aminoethyl)-tetraacetic acid (EGTA), ammonium molybdophosphate (AMP), triethanolamine (TEA), citrate, and nitrilotriacetic acid (NTA).

Embodiments of the present invention include methods of decontaminating a surface. A method comprises treating a surface to be decontaminated with a composition according to the present invention. Examples of contamination to be treated include, but are not limited to, biological, chemical, and radiological contamination.

A method of generating a foam is also disclosed. The method comprises providing a composition according to the present invention and injecting a gas into it so as to form a foam.

A method of decontaminating a surface with a foam is also disclosed. The method comprises generating a long-lasting decontamination foam with a composition according to the present invention. The method further comprises treating the surface to be decontaminated with the foam generated from the composition according to the present invention. The long-lasting nature of the foam generated by the decontaminating composition allows the application of cleaning agents and chemicals to surfaces, including vertical surfaces, and further allows a long period of contact between the surfaces and the decontamination composition.

EXAMPLES

Example I

Decontamination Compositions

A range of decontamination compositions were created in water. A variety of surfactants and potential foam stabilizers were tested. Reagents used included TRITON™ X-100 (T100), glycerin (GLY), sodium lauryl sulfate (SLS), potassium chloride (KCl), gelatin (gel), ethylene glycol, sodium stearate, potato starch, Ansul SILV-EX®, n-laurolysarcosine sodium (sarcosine LS), dioctyl sulfosuccinate sodium (sulfosuccinate DOS), and egg white (albumin).

Solutions created for testing are provided in Table 1 (all percentages indicate percentage of reagent by weight in the decontamination solution).

Where gelatin was used, it was not added directly to the solution as commercially available. Prior to being added to the decontamination solution, the gelatin was added to cold water and then heated to 200° F.

TABLE 1

0.1% SLS
1% SLS
0.01% SLS
0.5% sarcosine LS
0.5% sulfosuccinate DOS
1% T100/5% GLY
1% T100/1% SLS, 5% GLY, 0.5% KCl
3% T100/0.5% KCl
1% NH$_3$ LS, 0.5% KCl
1% SLS/3% GLY
1% SLS, 5% ethylene glycol
1% SLS, 2% gelatin
1% SLS 2% sodium stearate
1% SLS, 5% potato starch
1% SLS, 2% gelatin
0.5% Ansul SILV-EX ®
5% Ansul SILV-EX ®
1% Ansul SILV-EX ®, 3% gelatin
4% egg white (albumin)

Example 2

Foam Production and Decay

Screening of surfactants for foam making purposes was tested using a simple method. The American Society for Testing and Materials (ASTM-3601-88) technique of adding an aqueous solution of a surfactant to a glass bottle was used. The height of the solution in the bottle was measured. The bottle was vigorously shaken and the height of the top of the foam was recorded as a function of time. Aqueous solutions of 0.01% to 1% SLS, 0.5% sarcosine LS, 0.5% sulfosuccinate DOS, and 1% T100/0.5% KCl were tested. FIG. 1 graphically depicts the data for six different surfactants and/or concentrations.

Example 3

Short-Term Vertical Slip Tests

A range of decontamination compositions were used to generate foams. The foams were tested for their ability to adhere to a vertical surface with minimal slippage down the vertical surface over time. To generate the various foams, a glass frit was immersed into the decontamination compositions. Air was injected through the glass frit and into the solution at a pressure of 15 psi to 20 psi. The injection of air at this rate generated foam at a volume of approximately 6 to 8 liters/minute. The resulting foam was deposited onto a vertical marble block and the rate of slippage was determined after three minutes. The results of the short-term vertical slip tests are given in Table 2.

TABLE 2

| Decontamination Composition | Distance Traveled (mm for 3 min.) | % Relative Retention |
|---|---|---|
| 1% T100/5% GLY | 300 | 0 |
| 1% T100/1% SLS, 5% GLY, 0.5% KCl | 75 | 78 |
| 3% T100/0.5% KCl | 180 | 43 |
| 1% NH$_3$LS, 0.5% KCl | 300 | 0 |
| 1% SLS/3% GLY | 10 | 100 |
| 1% SLS, 5% ethylene glycol | 300 | 0 |
| 1% SLS, 2% gelatin | 300 | 0 |
| 1% SLS 2% sodium stearate | 300 | 0 |
| 1% SLS, 5% potato starch | 300 | 0 |
| 1% SLS, 2% gelatin | 300 | 0 |
| 0.5% Ansul | 100 | 70 |
| 5% Ansul | 70 | 80 |
| 1% Ansul, 3% gelatin | 10 | 100 |
| 4% egg white (albumin) | 300 | 0 |

T100 = TRITON ™ X-100, GLY = glycerin, SLS = sodium lauryl sulfate, KCl = potassium chloride, gel = gelatin, Ansul = Ansul SILV-Ex ® firefighting foam additive.

Example 4

Long-Term Vertical Slip Tests

The best performing decontamination compositions of Example 3 were used to generate foams for longer term testing. Again, the foams were tested for their ability to adhere to a vertical surface with minimal slippage down the vertical surface over time. To generate the various foams, a glass frit was immersed into the decontamination compositions. Air was injected through the glass frit and into the solution at a pressure of 15 psi to 20 psi. The injection of air at this rate generated foam at a volume of approximately 6 to 8 liters/minute. The resulting foam was deposited onto a vertical marble block and the rate of slippage was determined after 30 minutes. The results of the long-term vertical slip tests are given in Table 3.

TABLE 3

| Decontamination Composition | Distance Traveled (mm for 30 min.) | % Relative Retention |
|---|---|---|
| 1% SLS/3% GLY | 300 | 0 |
| 1% T100/1% SLS, 5% GLY, 0.5% KCl | decayed | 0 |
| 1% Ansul, 3% gelatin | 10 | 100 |

Example 5

Strong Acid Decontamination of Surfaces

A decontamination foam comprising 1% Ansul SILV-EX®, 3% gelatin, and 0.5 M HCl saturated with AMP and NTA, was created with a pH of approximately 0.3. The decontamination foam was applied to test coupons (both marble and concrete) that had been contaminated with a radionuclide. The decontamination foam was allowed to remain on the marble and concrete coupons for one hour. The marble and concrete coupons were then brushed, water rinsed and vacuumed to remove the decontamination foam. The marble and concrete coupons were then tested for residual radionuclide. After one hour, the 1 M HCl-containing foam was able to remove 82% of the radionuclide from the marble coupon and 20% of the radionuclide from the concrete coupon.

Example 6

Weak Acid Follow-on Decontamination of Surfaces

The test coupons of Example 5 were further treated with a decontamination foam comprising 1% Ansul SILV-EX®, 3% gelatin, and HOAc/NaOAc saturated with AMP and NTA and having a pH of approximately 4.5. The foam was allowed to remain on the coupons for four hours. The coupons were then brushed, water rinsed and vacuumed to remove the foam. The coupons were then tested for residual radionuclide. After one hour, the HOAc/NaOAc-containing foam was able to remove an additional 6% of the radionuclide from the marble coupon (for a total of 88%) and an additional 10% of the radionuclide from the concrete coupon (for a total of 30%).

What is claimed is:

1. A composition for decontamination consisting of:
   water, a surfactant, an acidifying agent, and gelatin;
   wherein the composition has a pH of less than 5; and
   wherein the composition is capable of generating a foam.

2. The composition of claim 1, wherein the surfactant is a fatty alcohol ether sulfate.

3. The composition of claim 2, wherein the fatty alcohol ether sulfate is sodium and ammonium salts of fatty alcohol ether sulfates.

4. The composition of claim 1, wherein the surfactant is present at about 0.1% to about 10% by weight.

5. The composition of claim 1, wherein the surfactant is present at 1% by weight.

6. The composition of claim 1, wherein the gelatin is present at about 1% to about 10% by weight.

7. The composition of claim 1, wherein the gelatin is present at 3 percent by weight.

8. The foam composition of claim 1, wherein the pH is between about −0.5 and 5.

9. The composition of claim 1, wherein the pH is selected from the group consisting of 0.3 and 4.5.

10. The composition of claim 1, wherein the foam generated from the composition slips 10 mm down the vertical surface of a marble block in three minutes.

11. The composition of claim 1, wherein the foam generated from the composition slips 10 mm down the vertical surface of a marble block in 30 minutes.

12. A method of decontaminating a surface comprising:
   providing a composition for decontamination, the composition consisting of:
   water, a surfactant, an acidifying agent, and gelatin;
   wherein the composition has a pH of less than 5; and
   wherein the composition is capable of generating a foam; and
   treating the surface to be decontaminated with the composition.

13. The method of claim 12, wherein the surfactant is a fatty alcohol ether sulfate.

14. The method of claim 13, wherein the fatty alcohol ether sulfate is selected from sodium and ammonium salts of fatty alcohol ether sulfates.

15. The method of claim 12, wherein the surfactant is present at about 0.1% to 10% by weight of the composition.

16. The method of claim 12, wherein the surfactant is present at about 1% by weight of the composition.

17. The method of claim 12, wherein the gelatin is present at about 1% to 10% by weight of the composition.

18. The method of claim 12, wherein the gelatin is present at about 3 percent by weight of the composition.

19. The method of claim 12, wherein the pH is between about −0.5 and 5.

20. The method of claim 12, wherein the pH is selected from the group consisting of 0.3 and 4.5.

21. The method of claim 12, wherein the foam generated from the composition slips 10 mm down the vertical surface of a marble block in three minutes.

22. The method of claim 12, wherein the foam generated from the composition slips 10 mm down the vertical surface of a marble block in 30 minutes.

23. A composition for decontamination consisting of:
   water, a surfactant, an acidifying agent, an affinity-shifting chemical, and gelatin;
   wherein the composition has a pH of less than 5; and
   wherein the composition is capable of generating a foam.

24. The composition of claim 23, wherein the affinity-shifting chemical is selected from the group consisting of EDTA, AMP, NTA, and a combination of acetic acid and sodium acetate.

25. A method of decontaminating a surface comprising:
   providing a composition for decontamination, the composition consisting of:
   water, a surfactant, an acidifying agent, an affinity-shifting chemical, and gelatin;
   wherein the composition has a pH of less than 5; and
   wherein the composition is capable of generating a foam; and
   treating the surface to be decontaminated with the composition.

26. The method of claim 25, wherein the affinity-shifting chemical is selected from the group consisting of EDTA, AMP, NTA, and a combination of acetic acid and sodium acetate.

* * * * *